United States Patent [19]
Ogata et al.

[11] Patent Number: 5,480,773
[45] Date of Patent: Jan. 2, 1996

[54] METHOD FOR PRESERVING BLOOD USING ASCORBIC ACID TOCOPHERYL PHOSPHATE ESTERS

[75] Inventors: Kazumi Ogata, Osaka; Kenichi Yoshida, Kobe, both of Japan

[73] Assignee: Senju Pharmaceutical Co., Ltd., Osaka, Japan

[21] Appl. No.: 301,387

[22] Filed: Sep. 7, 1994

Related U.S. Application Data

[63] Continuation of Ser. No. 121,372, Sep. 15, 1993, abandoned.

[30] Foreign Application Priority Data

Sep. 30, 1992 [JP] Japan .................... 4-261311

[51] Int. Cl.⁶ .................... A01N 1/02
[52] U.S. Cl. .................... 435/2; 424/529
[58] Field of Search .................... 435/2; 424/529

[56] References Cited

U.S. PATENT DOCUMENTS

| | | | |
|---|---|---|---|
| 4,605,644 | 8/1986 | Foker | 514/45 |
| 4,994,444 | 2/1991 | Zikria | 514/60 |
| 5,256,642 | 10/1993 | Fearon et al. | 514/8 |

FOREIGN PATENT DOCUMENTS 324387  7/1989  European Pat. Off. .

OTHER PUBLICATIONS

Kopeć–Szlezak J et al, Haematologia 21: 219–226 (1988).

*Primary Examiner*—Irene Marx
*Assistant Examiner*—Sandra Saucier
*Attorney, Agent, or Firm*—Wenderoth, Lind & Ponack

[57] ABSTRACT

A method for the preservation of blood and a blood preserving composition comprising a phosphoric acid diester of the following formula:

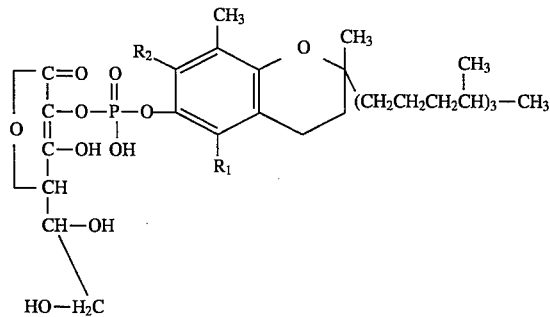

(wherein $R_1$ and $R_2$ are the same or different and each represents a hydrogen atom or a methyl group) or a pharmacologically acceptable salt thereof.

The compounds used for the object of the invention are capable of maintaining the biological function of blood for a long period of time without harming its components. Therefore, the composition of the invention can be advantageously used for preserving blood and its components such as erythrocytes, leukocytes and platelets, and is useful for preventing hepatic disorder which can accompany blood transfusion.

1 Claim, No Drawings

METHOD FOR PRESERVING BLOOD USING ASCORBIC ACID TOCOPHERYL PHOSPHATE ESTERS

This application is a continuation of now abandoned application Ser. No. 08/121,372, filed Sep. 15, 1993.

BACKGROUND OF THE INVENTION

1. Field of the Invention

The present invention relates to a method for the preservation of blood and to a useful blood preserving composition. More particularly, the invention relates to the preservation of blood by incorporating a phosphoric acid diester of ascorbic acid and tocopherol, or a pharmacologically acceptable salt thereof.

2. Description of the Prior Art

Blood consists of formed elements such as erythrocytes, leukocytes and platelets and plasma which is the liquid component in which the formed elements are contained. Blood is a vital medium for the life of the body cells and its properties remain almost constant. In the meantime, during surgery and in other cases, the transfusion of blood or its components is oftentimes required. The biological functions of blood or its components must be maintained while in storage and until the transfusion is accomplished. It is also of importance to prevent functional disorders such as hepatic disorder, which can sometimes accompany blood transfusion.

As employed herein, the term "blood" is intended to encompass not only "whole" blood but also its component parts as indicated above.

Compositions for preserving blood have been previously known. For these purposes, there have chiefly been used sugars as an energy source, inorganic salts as agents for adjusting pH and osmotic pressure, and adenine as an agent for preventing consumption of blood ATP (adenosine triphosphate), ADP (adenosine diphosphate) and AMP (adenosine monophosphate). However, these blood preserving compositions are hardly satisfactory because they cannot fully maintain blood ATP level which is an index of life for the haemocyte components and because they do not have a satisfactory preventive activity against hepatic disorders which have been associated with blood transfusion.

Accordingly, blood preserving compositions which have a superior blood preserving action and preventive activity against potential hepatic disorders after blood transfusion are presently under study.

Under the circumstances, the inventors of the present invention have searched for compounds having potent blood preserving activity and have found that a phosphoric acid diester of ascorbic acid and tocopherol and pharmacologically acceptable salts thereof have a potent blood preserving action. Based on the above finding, the present invention has been completed.

SUMMARY OF THE INVENTION

The present invention is, therefore, directed to an improvement in blood preserving compositions, said improvement comprising incorporating thereinto a phosphoric acid diester of the following formula:

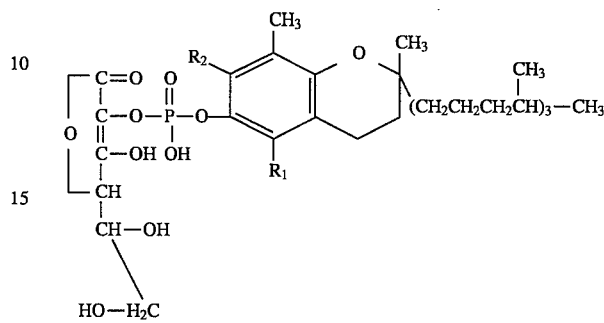

(wherein $R_1$ and $R_2$ are the same or different and each represents a hydrogen atom or a methyl group) or a pharmacologically acceptable salt thereof (hereinafter referred to briefly as the Compound).

DETAILED DESCRIPTION OF THE INVENTION

Unless contrary to the context, the term "blood" used herein means "whole" blood itself and its components such as erythrocyte, leukocyte and platelet.

The Compound, which is used for the blood preserving composition of the invention and represented by the above formula, can be produced by the methods described in, among others, Japanese Patent Kokoku No. Hei-2-44478 and Japanese Patent Kokai No. Sho-62-205091 or by their modified methods.

The Compound represented by the above formula, either the free acid form or a pharmacologically acceptable salt thereof, can be used for the object of the present invention. The salt may be an alkali metal salt such as the sodium salt and the potassium salt, or an alkaline earth metal salt such as the calcium salt and the magnesium salt.

The Compound used for the blood preserving composition of the invention is already known as, among others, an anticataract agent, a prophylactic and therapeutic agent for climacteric disturbance, a skin-beautifying cosmetic (Japanese Patent Kokoku No. Hei-2-44478), an anti-inflammatory drug (Japanese Patent Kokoku No. Hei-1-27044), an antiulcer drug (Japanese Patent Kokai No. Sho-63-270626) and a prophylactic and therapeutic agent for ischemic disorder in organs (Japanese Patent Kokai No. Hei-2-111722). It has not been known, however, that the Compound is useful for preserving blood, which is the object of the invention.

The blood preserving compositions of the invention may contain one or more species of the Compound or its salts thereof in suitable combination according to the object and need.

In preserving blood, the blood preserving composition of the invention can be used in the form of a liquid, i.e., solution, suspension or emulsion. The blood preserving composition of the invention may initially be formulated into either a liquid composition or a solid composition, and the solid composition may be formulated into a liquid composition for use. The solid composition may be dissolved, suspended or emulsified in purified water or physiological saline and so on. As to the solid composition, tablets, granules and powders are exemplified and can be adequately manufactured by conventional methods. As the case may be, these solid compositions as such can be contained in blood or its components.

The blood preserving composition of the invention may contain conventional ingredients used for blood preserving compositions, such as blood coagulation inhibitory drugs, nutritive agents, isotonizing agents, pH adjusting agents, preservatives, solubilizers and thickeners in conventional proportions. These ingredients may include, for example, sugars, salts, amino acids, nucleic acid bases and organic acids. The sugars include, among others, sucrose, glucose, lactose, dextrose and mannitol. As to the salts, sodium chloride, sodium citrate, sodium phosphate are exemplified. As to the amino acids, glycine, glutamic acid and lysine are exemplified. As to the nucleic acid base, adenine is exemplified. Furthermore, as to the organic acid, citric acid, acetic acid and lactic acid are exemplified.

Unless contrary to the object of the present invention, the blood preserving composition of the invention can be supplemented with other active ingredients, for example, antibiotics or hepatic impairment inhibitory drugs.

The blood preserving composition of the invention is capable of maintaining the biological function of blood for a long period of time without harming its components. Therefore, the composition of the invention can be advantageously used for preserving blood and its components such as erythrocytes, leukocytes and platelets, and is useful for preventing hepatic disorder which oftentimes accompanies blood transfusions.

The Compound employed in the blood preserving composition of the invention has very low toxicity and is highly safe, so that it can be advantageously used for blood preservation and blood transfusion. [$LD_{50}$ of the sodium salt of phosphoric acid diester of L-ascorbic acid, DL-α-tocopherol (hereinafter referred to briefly as EPC-Na): Per os>10 g/kg (rat), Subcutaneous administration>793 mg/kg (rat)].

In carrying out the method of the invention, the Compound is incorporated into and mixed with the blood or a composition containing one or more species of the blood components. More particularly, the method for the preservation of blood is carried out in the following manner or by its modified methods. To blood just collected are added appropriate amounts of blood coagulation inhibitory drugs such as citric acid, its salt, heparin and sodium edetate and a blood preserving effective amount of the Compound, and then the composition is admixed under cooling. From the mixture thus prepared, the intended blood component or fraction is separated by centrifugation at about 4,000 to 4,500 g for about 5 to 10 minutes and then collected by conventional methods. Upon necessity, to each blood component or fraction is further added a certain amount of the blood preserving composition of the invention. Then, each composition thus obtained is stored in a container under cooling.

The dosage of the Compound for the purpose of the invention varies according to the species of the Compound employed, the preservation temperature, the intended preservation time and so forth. As the final concentration of the Compound in blood, it is usually in the range of about $5 \times 10^{-9}$ g/ml to about $5 \times 10^{-3}$ g/ml, preferably about $5 \times 10^{-8}$ g/ml to about $5 \times 10^{-5}$ g/ml.

In formulating into a liquid composition, the osmotic pressure of the blood preserving composition may be adjusted to about 0.5 to 5 (pressure ratio), preferably about 0.8 to 2 (pressure ratio) by conventional methods. The pH of the liquid composition may be adjusted to about 3 to 10, preferably about 4 to 9 by conventional methods.

In preserving blood by using the blood preserving composition of the invention, the temperature depends on the Compound to be used, its amount and the intended preservation time and so on, but it is usually in the range of about −5° C. to 20° C., preferably about 0° C. to 15° C.

In preserving blood by using the blood preserving composition of the invention, any conventional container for preserving blood, for example, plastic bags and glass bottles, can be adequately used.

EXAMPLES

The following experimental and working examples are intended to describe the invention in further detail.

EXPERIMENTAL EXAMPLE 1

The Effect of the Compound on Blood Preservation

Test Compound

Potassium salt of phosphoric acid diester of L-ascorbic acid, DL-α-tocopherol (hereinafter referred to briefly as EPC-K).

Method

Heparin-treated human blood was allowed to stand at 20° C. for 15 minutes and then separated into plasma and haemocyte by centrifugation at 3,000 rpm for 5 minutes. To three volumes of physiological saline and three volumes of electrolyte solution for infusion ["SOLITA-T No. 2" (Registered Trademark)" produced by Shimizu Seiyaku Co.], was added one volume of the haemocyte separated respectively. To each solution was further added EPC-K in its final concentrations of $5 \times 10^{-5}$ g/ml to $5 \times 10^{-7}$ g/ml. Then, the solutions containing EPC-K and the ones with no EPC-K added were stored at 4° C. for 5 days. The ATP (adenosine triphosphate) level, ADP (adenosine diphosphate) level and AMP (adenosine monophosphate) level in the haemocyte were determined by the HPLC method, and then the energy charge (E.C.) (%) in the haemocyte was calculated from the following formula.

$$E.C. \ (\%) = \frac{ATP \text{ level} + {}^{1/2} \times ADP \text{ level}}{ATP \text{ level} + ADP \text{ level} + AMP \text{ level}} \times 100$$

Results

The energy charge determined immediately after the collection of blood was 54.2%. The energy charge after storing for 5 days at 4° C. is shown in Table 1.

TABLE 1

| | Energy Charge (%) | |
| --- | --- | --- |
| EPC-K (g/ml) | Physiological saline 19.6 | Electrolyte solution for infusion 23.4 |
| $5 \times 10^{-5}$ | 52.7 | 37.6 |

TABLE 1-continued

| | Energy Charge (%) | |
|---|---|---|
| EPC-K (g/ml) | Physiological saline 19.6 | Electrolyte solution for infusion 23.4 |
| $5 \times 10^{-6}$ | 48.0 | 53.1 |
| $5 \times 10^{-7}$ | 48.8 | 39.7 |

From these results it can be seen that EPC-K proved to be useful for preserving blood since the energy charge in the haemocyte, which represents an index of life, was maintained.

EXAMPLE 1

The following ingredients were formulated into a sterile liquid composition:

| EPC-Na | 2 mg |
|---|---|
| Mannitol | 55 g |
| Sodium dihydrogenphosphate | 1 g |
| Citric acid | 1 g |
| Adenine | 0.3 g |
| Sodium hydroxide | q.s. |
| hydrochloric acid | q.s. |
| Sterile purified water | Total 1,000 ml pH 7 |

About 40 ml of the above composition containing citric acid which is a blood coagulation inhibitory drug were added into about 200 ml of blood just collected, and then admixed gently. From the mixture thus obtained, under cooling, the haemocyte fraction was separated by centrifugation at 4,500 g for 10 minutes and then collected. Then, about 70 ml of the haemocyte fraction thus obtained, which contain EPC-Na, were stored in a PVC bag at 4° C. for 7 days in the absence of atmospheric oxygen.

EXAMPLE 2

The following ingredients were formulated into a sterile-liquid composition:

| EPC-K | 20 mg |
|---|---|
| Mannitol | 25 g |
| Sodium dihydrogenphosphate | 500 mg |
| Adenine | 0.2 g |
| Sodium chloride | 4.5 g |
| Sodium hydroxide | q.s. |
| hydrochloric acid | q.s. |
| Sterile purified water | Total 1,000 ml pH 7 |

What is claimed is:

1. In a method for the preservation of ATP level or energy charge in haemocytes which comprises admixing the haemocytes with a preserving composition therefor, the improvement comprising adding to the preserving composition, a haemocytes' ATP level or energy charge preserving effective amount of a phosphoric acid diester of the following formula:

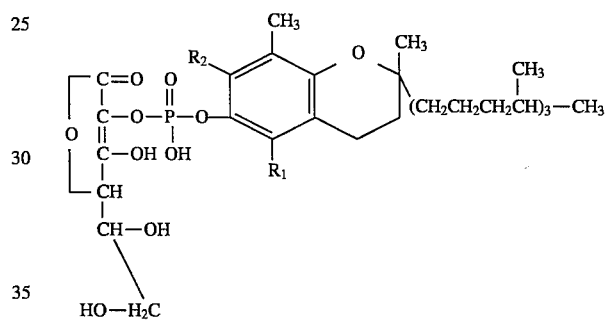

wherein $R_1$ and $R_2$ are the same or different and each is a hydrogen atom or a methyl group or a pharmacologically acceptable salt thereof.

* * * * *